United States Patent
Yanez Reyes

(10) Patent No.: US 10,342,237 B2
(45) Date of Patent: Jul. 9, 2019

(54) PLANT AND GROWTH DEVELOPMENT, INDUCTIVE RESISTANCE BIO-STIMULANT FORMULATION FOR PHYTOPATHOGEN VIRUS INDUCED DISEASE CONTROL AND METHOD OF PREPARATION

(71) Applicant: GREENCORP BIORGANIKS DE MEXICO S.A. DE C.V., Saltillo, Coahuila (MX)

(72) Inventor: Jesus Noel Yanez Reyes, Coahuila (MX)

(73) Assignee: GREENCORP BIORGANIKS DE MEXICO S.A. DE C.V., Saltillo, Coahuila (MX)

( * ) Notice: Subject to any disclaimer, the term of this patent is extended or adjusted under 35 U.S.C. 154(b) by 0 days.

(21) Appl. No.: 15/297,941

(22) Filed: Oct. 19, 2016

(65) Prior Publication Data

US 2017/0215433 A1     Aug. 3, 2017

(30) Foreign Application Priority Data

Feb. 2, 2016    (MX) .................... MX/a/2016/001466

(51) Int. Cl.

| | | |
|---|---|---|
| A01N 37/40 | (2006.01) | |
| A01N 37/46 | (2006.01) | |
| A01N 39/02 | (2006.01) | |
| A01N 43/78 | (2006.01) | |
| A01N 59/02 | (2006.01) | |
| A01N 65/00 | (2009.01) | |
| A01N 65/08 | (2009.01) | |
| A01N 65/10 | (2009.01) | |
| A01N 65/22 | (2009.01) | |
| A01N 65/42 | (2009.01) | |

(52) U.S. Cl.
CPC ............. *A01N 65/22* (2013.01); *A01N 37/40* (2013.01); *A01N 37/46* (2013.01); *A01N 39/02* (2013.01); *A01N 43/78* (2013.01); *A01N 65/00* (2013.01); *A01N 65/08* (2013.01); *A01N 65/42* (2013.01)

(58) Field of Classification Search
None
See application file for complete search history.

(56) References Cited

U.S. PATENT DOCUMENTS

| 4,435,203 | A | * | 3/1984 | Funaki | ................. | A01N 43/653 |
|---|---|---|---|---|---|---|
| | | | | | | 504/181 |
| 8,202,557 | B1 | | 6/2012 | Doty | | |
| 8,529,968 | B2 | | 9/2013 | Belbachir et al. | | |
| 2006/0194698 | A1 | | 8/2006 | Gwinn et al. | | |
| 2008/0125320 | A1 | * | 5/2008 | Coats | ........................ | A01N 3/00 |
| | | | | | | 504/116.1 |
| 2010/0162620 | A1 | * | 7/2010 | McCaffrey | ............. | A01G 33/00 |
| | | | | | | 47/1.4 |
| 2014/0364309 | A1 | | 12/2014 | Hellwege et al. | | |

FOREIGN PATENT DOCUMENTS

| WO | 8909200 A1 | 10/1989 |
|---|---|---|
| WO | 2006097700 A1 | 9/2006 |
| WO | 2012045189 A2 | 4/2012 |
| WO | 2013030422 A1 | 3/2013 |
| WO | 2014020187 A1 | 2/2014 |

OTHER PUBLICATIONS

Difference between Absolutes and Essential Oils [online]. Aromatherpay at Home Nov. 14, 2007 [retirieved on Aug. 30, 2017]. Retrieved from the internet: <http://www.aromatherapy-at-home.com/differencebetweenabsolutesandessential.html>.*

What Kinds of Vitamins Do Plants Need? [online]. Homeguides, Jun. 16, 2013 [retrieved on Aug. 29, 2017]. Retrieved from the internet: <http://homeguides.sfgate.com/kinds-vitamins-plants-need-49591.html>.*

*Mentha spicata* L. [online]. USDA Natural Resources Convservation Service, Sep. 6, 2014 [retrieved on Aug. 30, 2017]. retrieved from the internet <https://plants.usda.gov/core/profile?symbol=MESP3>.*

Chivahuan Desert Plants [online], Jun. 15, 2010 [retrieved on Aug. 29, 2017]. Retrieved from the internet: <http://museum2.utep.edu/chih/gardens/list/species.htm>.*

Southern North America: Northern Mexico into southwestern United States [online]. Worldwildlife, May 1, 2013 [retrieved on Aug. 29, 2017]. Retrieved from the internet: <https://www.worldwildlife.org/ecoregions/na1303>.*

* cited by examiner

*Primary Examiner* — Katherine Peebles
(74) *Attorney, Agent, or Firm* — Lucas & Mercanti, LLP

(57) ABSTRACT

The present invention refers to a plant growth and development, inductive resistance bio-stimulant formulation for phytopathogen virus disease control and its method of preparation from plant extracts and other natural origin products. The plant growth and development, inductive resistance bio-stimulant formulation for phytopathogen virus disease control is composed of plant extracts and vegetable oils proceeding from Chihuahua semi-desert plant varieties and absolute oils and aromatic plant extracts, and other components. This formulation has been widely proven in field and is useful for phytopathogen virus disease control, preventing and reducing DNA and RNA virus damage of greater impact in vegetable and fruit crop production, ameliorating the number of damaged plants, delaying the appearance of virosis symptoms, significantly decreasing the severity of damage, reducing virus dissemination in plantation, favoring growth continuity in plant and assuring a greater yield under attack conditions.

11 Claims, 9 Drawing Sheets

Day 0    Day 8    Day 18

|       | − | + | kb | 1 | 4 | 5 | 8 | 9 | 20 | 28 | 38 | 40 | 46 |        |
|-------|---|---|----|---|---|---|---|---|----|----|----|----|----|--------|

ToMarV                                                                      517 pb

Nested
ToMarV                                                                      320 pb Day 0

|       | − | + | kb | 1 | 4 | 5 | 8 | 9 | 20 | 28 | 38 | 40 | 46 |        |
|-------|---|---|----|---|---|---|---|---|----|----|----|----|----|--------|

ToMarV                                                                      517 pb

Nested
ToMarV                                                                      320 pb Day 36

PLANT AND GROWTH DEVELOPMENT, INDUCTIVE RESISTANCE BIO-STIMULANT FORMULATION FOR PHYTOPATHOGEN VIRUS INDUCED DISEASE CONTROL AND METHOD OF PREPARATION

CROSS REFERENCE TO RELATED APPLICATION

This application claims priority of Mexican Patent Application No. MX/A/2016/001466 filed Feb. 2, 2016, which is incorporated herein by reference.

TECHNICAL FIELD OF THE INVENTION

The present invention refers to biotechnology area and particularly concerns to the field of agricultural biotechnology. It relates to the use of plant extracts and other natural origin products to prepare a growth and plant development, inductive resistance bio-stimulant formulation for control of diseases caused by phytopathogen virus.

BACKGROUND OF THE INVENTION

Plant diseases are the cause of major economic losses in agriculture around the world (Martinelli et al., 2015). Viruses cause many diseases in plants of international importance and are responsible for great losses in terms of production and quality in crops; although difficult to calculate those economic losses those are considered to represent more than 30 billion dollars per year (Sastry and Zitter, 2014).

Viruses are strictly intra-cellular pathogens whereby their control is complicated and the main measures for their control are bound to destruction of infected plants or an excessive use of pesticides for the control of organisms that work like virus vectors (Nicaise, 2014). Antiviral compounds capable to cure viral diseases in plants practically are nonexistent and present control measures can only mitigate or prevent their occurrence (Gergerich and Dolja, 2006).

The first step required for handling viral diseases is the identification of virus. The strategy of subsequent handling will depend on the form by which a certain virus is introduced into any crop, how the virus is transmitted between the plants of the same crop, and how the virus survives in the absence of the crop (Haddidi et al., 1998). Some preventive measures include the use of virus-free certified seeds or vegetative organs, elimination of possible virus reservoirs in the surrounding wild vegetation and the modification of sowing and harvest practices. If the virus has any known transmission vector, vector control or exclusion is extremely important, for example: nematodes, insect and fungus vectors that can be controlled with nematicides, insecticides and fungicides, respectively (Gergerich and Dolja, 2006).

Nevertheless, an alternative for virus control may be found in own plant evolution which has provided resistance mechanisms through plant-virus interactions. In the last decades, processes for identification and understanding of phytohormone role and other key components in plant response to biotic stress have been developed (Robert-Seilaniantz et al., 2011). Starting from this idea, diverse natural origin ingredients may be selected to integrate an alternative to induce plant defense for virus damage through the activation of acquired systemic resistance mechanisms (Delaney et al., 1994).

Traditionally the use of diverse plant extracts with a number of applications has been described, being one of them product development with plant extracts allowing a favorable plant development, as well as resistance induction against diverse phytopathogens. Thus, several technologies have been described in the state-of-the-art, as described in international patent application WO 1989009200 A1 referred to the use of *Viscum* álbum or white mistletoe extract as part of a composition for soil conditioning and leaf fertilizer allowing nutrient restoring in soil and regeneration thereof. Moreover, the use of *Viscum* álbum extracts has been reported also in combination with other active compounds or extracts, such as in United States patent application No. 2014/0364309 A1 wherein *Aloe vera* and seaweed extracts are used to reduce damage in plants and their fruits caused by insects, parasites and other phytopathogens excluding virus.

International patent application WO2006097700 A1 refers to individual or combined use of plant essential oils such as eucalyptus (*Eucalyptus globulus*), spearmint (*Mentha piperita*), clove (*Syzygium aromaticum*) or marjoram (*Lippia graveolens*), in combination with vegetable oil and an emulsifier agent to improve plant growth. Similarly, several United States patent documents disclose the use of *Coriandrum sativum* extracts with a number of applications: the first one, U.S. Pat. No. 8,202,557 B, has been used to prepare insecticides, whereas in U.S. patent application 2006/0194698 A1 reference is made to active phytochemicals to protect plants from weeds, plagues and phytopathogens; and although antiviral properties for *Coriandrum sativum* extracts have been also described as in U.S. Pat. No. 8,529,968 B2, those have not been linked to phytopathogen virus.

On the other hand, in recent years and due to a demand of products allowing plant growth stimulation as well as increasing at the same time the protection spectrum against pathogens (virus, bacteria and fungi) a series of chemical compounds have been developed, as well as a new generation of products so-called bio-stimulants, which contains diverse substances and/or microorganisms which when applied to plants or the rhizosphere they improve crop development and biotic stress responses. Some bio-stimulants are described in international patent applications WO 2014020187 A1, WO 2013030422 A1 and WO 2012045189 A2 where in the first one bio-stimulants are prepared from mineral or animal origin compounds and seaweed extracts; in WO 2013030422 A1 patent application, residues coming from beer manufacturing for bio-stimulant production are used; whereas in WO 2012045189 A2 application, bio-stimulants are made from chitosan and *Saccharomyces cerevisae* hydrolysate.

Although a wide use of diverse plant extracts and plant essential oils with antiviral activity has been described, only a few have been tested directly on agricultural crops and specifically with phytopathogen virus.

Some other bio-stimulant products that are currently in market are made from glutathione, oligosaccharins and combinations of plant extracts and oils which provide certain effectiveness in fighting viruses, however none of them describes a combination of extracts and substances comprising present invention and which allow to have a synergistic effect for fighting DNA and RNA virus of higher impact on vegetable and fruit crop production. Some of the main technical advantages of the invention are as follows: prevention and reduction of virus damage, reduction of damaged plants, delay of appearance of virosis symptoms, a significant decrease in damage severity, a reduction of virus dissemination in the plantation, favoring the continuity of the plant growth and assures a higher yield under attack conditions.

In view of the state of the art background, the technical problem that solves the present invention is to provide a base formulation on the use of diverse plant extracts and plant essential oils to make a bio-stimulant action product for plant growth and development and phytopathogen virus inductive resistance, showing characteristics to be sustainable for safe application and for vertebrate and invertebrate health and environment low impact, which causes that present invention is novel, inventive and with a clear application in the field of agriculture.

SUMMARY OF THE INVENTION

An object of the present invention is to provide a base formulation on the use of diverse plant extracts and plant essential oils to make a product with agronomic application. Such plant extracts and essential oils comprising: ethanolic and acetone extracts of *Larrea tridentata, Viscum* album ethanol extracts, *Lippia graveolens* absolute oils and *Euphorbia antisyphilitica, Jatropha dioica* and *Agave Americana* hexane extracts, *Syzygium aromaticum* and *Cinnamomum zeylanicum* oils, *Eucalyptus globulos* methanolic extract, *Rosmarinus officinalis, Salvia officinalis* and peppermint aqueous extracts, and *Coriandrum sativum* ethanolic extract. Additionally, the formulation includes sulfured compounds, aminoacids and specific peptides of plant and animal origin, hormones and plant growth regulators, multivitamins and polysaccharides.

Another subject of the invention is to provide a formulation with bio-stimulant activity for growth and plant development, mainly in plants of the families Solanaceae, Cucurbitaceae, Rosaceae, Leguminosae, Alliaceae, Caricaceae, and Musaceae, among others of commercial interest.

Another subject of the present invention is to provide an alternative to damage prevention and reduction associated to plant diseases caused by phytopathogen virus.

An additional subject of the present invention is to provide an alternative to induce plant resistance to diseases caused by RNA- and DNA-type phytopathogen viruses.

Another subject of the present invention includes providing a process of preparation of a plant growth and development, inductive resistance bio-stimulant formulation for control of diseases caused by phytopathogen viruses.

BRIEF DESCRIPTION OF THE DRAWINGS

FIG. 13 shows images of agarose gel electrophoresis for RNA virus detection analysis of Torradovirus genus (ToMarV) in tomato crop plants at the beginning (Day 0) and 36 days after evaluation.

FIG. 14 shows images of agarose gel electrophoresis for RNA virus detection analysis of Torradovirus genus (ToMarV) in pepper crop plants at the beginning (Day 0) and 36 days after evaluation.

DETAILED DESCRIPTION OF THE INVENTION

Figure 1:
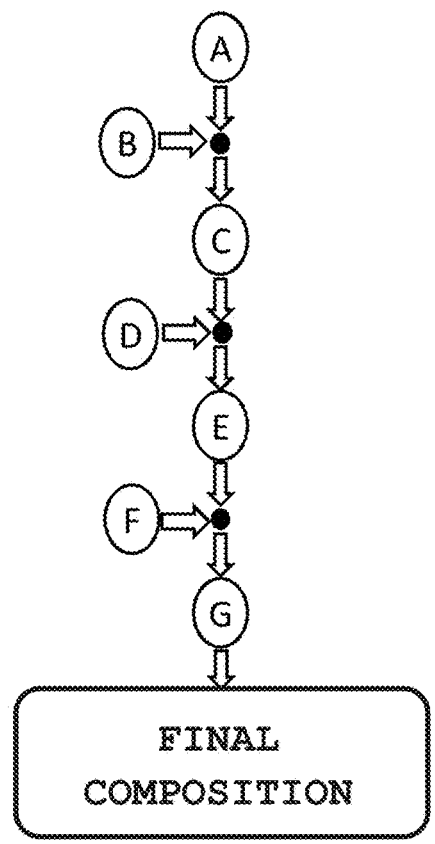
FIG. 1 shows a process diagram for preparation of the plant growth and development, inductive resistance bio-stimulant formulation for control of diseases caused by phytopathogen viruses subject of the present invention that is formed by To-G stages.

The approach of the invention concerns to the use of extracts and plant oils prepared from leaves, roots, stems and crust from regional specific biotype of Chihuahua semi-desert endemic and wild plants, to design a formulation with plant growth bio-stimulant action and phytopathogens virus inductive resistance by providing local resistance and Systemic Acquired Resistance (RSA) promoter phytomolecules in virus infected plants.

The subject formulation of the present invention consists of a mixture of multiple extracts of plant species that are not attacked by virus thus taking advantage of diverse properties that impact in the final formulation as active compounds are present in crusts, stems, roots and leaves of these species.

The plant growth and development, inductive resistance bio-stimulant formulation for phytopathogen virus disease control, subject of the present invention includes essentially the following components:

a) Extracts and plant oils from Chihuahua semi-desert plant varieties, such as: *Larrea* tridentate ethanolic and acetone extracts, *Viscum album* ethanolic extract, *Lippia graveolens* absolute oil and *Euphorbia antisyphilitica, Jatropha dioica* and *Agave Americana* hexane extracts.

b) absolute oils and extracts of aromatic plants, such as *Syzygium aromaticum* and *Cinnamomum zeylanicum* oils, *Eucalyptus globulos* methanolic extract, *Rosmarinus officinalis, Salvia officinalis* and peppermint aqueous extracts, and *Coriandrum sativum* ethanolic extract.

c) Sulfur compounds, amino acids and specific peptides of plant and animal origin such as: sulfathiazole, sodium lauryl sulfate, calcium thiosulfates, phenylalanine, soy milk and egg white peptides.

d) hormones and plant growth regulators like auxins, gibberellins, salicylic acid, jasmonates, their precursors, derivatives and salts, and the like.

e) Vitamins and polysaccharides provided by *aloe vera* gel.

In order to obtain different extracts that comprise the invention described conventional methods in the state-of-the-art are used.

Preparation of the plant growth and development, inductive resistance bio-stimulant formulation for phytopathogen virus disease control consists adding the components verifying that each is properly dissolved and homogenous before continuing to the aggregation of the following material. Preparation is carried out in constant stirring and when performed in such way exothermal reactions are neither caused nor any type of induction is required. Due to the physicochemical nature of some of its components, it is necessary to prepare some premixes separately to favor its incorporation into the final formulation. In order to prepare the formulation, components are added slowly and orderly as described below and as outlined in FIG. 1. Concentrations of each component of the plant growth and development, inductive resistance bio-stimulant formulation for phytopathogen virus disease control are further reported. The process considers the following stages (FIG. 1):

A) Preparation of the formulation base initially composed of aqueous extracts and water soluble components. The base formulation components are as follows which are added in sequential order:
   aqueous extract of *Rosmarinus officinalis* (0.75-1.25% v/v)
   aqueous extract of Peppermint (0.75-1.25% v/v)
   aqueous extract of *Salvia officinalis* (0.75-1.25% v/v)
   Soymilk (1.5-2.5% v/v)
   Egg White (0.75-1.25% v/v)
   *Aloe vera* gel (0.75-1.25% v/v)
   Sulfathiazole (0.375-0.625% w/v)
   Phenylalanine (0.75-1.25% w/v)
   Calcium thiosulfate (15.0-25.0% w/v)

B) Preparation of Premix 1, comprising the medium-high polarity components: ethanolic plant extracts, hormones and plant growth regulators such as auxins, gibberellins, salicylic acid, its precursors, derivatives and salts, and the like:
   Ethanolic extract of *Larrea tridentata* (0.75-1.25% v/v)
   Ethanolic extract of *Viscum álbum* (0.75-1.25% v/v)
   Ethanolic extract of *Coriandrum sativum* (0.75-1.25% v/v)
   Naphthoxyacetic acid (0.15-0.25% w/v)
   6 Benzylaminopurine (0.225-0.375% w/v)
   Salicylic acid (1.5-2.5% w/v)

C) Premix 1 is added to the base formulations with constant stirring. Other components of average polarity are later added, as:
   *Eucalyptus globulus* methanolic extract (0.75-1.25% v/v)

D) Preparation of Premix 2, comprising absolute oils:
   *Syzygium aromaticum* oil (0.75-1.25% v/v)
   *Cinnamomum zeylanicum* oil (0.75-1.25% v/v)
   *Lippia graveolens* oil (0.75-1.25% v/v)

E) Premix 2 is added to the base formulation on constant stirring. Other average polarity components of are added such as:
   *Larrea tridentate* acetone extract (0.75-1.25% v/v)

F) Preparation of Premix 3 comprising lower polarity extracts (hexane extracts), such as:
   *Euphorbia antisyphilitica* hexane extract (0.75-1.25% v/v)
   *Jatropha dioica* hexane extract (0.75-1.25% v/v)
   *Agave americana* L crust hexane extract (0.75-1.25% v/v)

G) Addition of Premix 3 to the base formulations with constant stirring for obtaining the final formulation. A conditioner agent such as sodium lauryl sulfate is used in order to prepare the formulation (7.5-12.5% w/v).

Once the plant growth and development and inductive resistance bio-stimulant formulation for phytopathogen virus disease control is obtained, this is properly packaged and stored for its use.

Obtained formulation, with plant growth and development and inductive resistance bio-stimulant activity for phytopathogen virus disease control prevents and reduces high impact DNA and RNA virus damage in the production of vegetable and fruit crops, ameliorates the number of damaged plants, delays the appearance of virosis symptoms, decreases significantly the damage severity, reduces the dissemination of virus in plantation, favors growth continuity in plants and assures a higher yield under attack conditions. Applications of the subject formulation of the invention are verified in diverse tests performed for phytopathogen virus control in different plant species.

EXAMPLES

The present invention illustrates the following examples which include but are not limited to:

Example 1

Preparation of the Formulation

In order to prepare a 1000 L batch of the plant growth and development, inductive resistance bio-stimulant formulation for phytopathogen virus disease control, components proceeded to be mixed in purified water according to the previously described process which is outlined in FIG. 1 diagram, maintaining constant stirring between adding one component and another. The components and the amounts specifically used for this example are enlisted below:
   *Rosmarinus officinalis* aqueous extract (9 L)
   Peppermint aqueous extract (7.5 L)
   *Salvia officinalis* aqueous extract (7.5 L)
   Soymilk (25 L)
   Egg white (7.5 L)
   *Aloe vera* gel (10 L)
   Sulfathiazole (4.5 kg)
   Phenylalanine (0.8 kg)
   Calcium thiosulfate (150 kg)

Premix 1:
*Larrea tridentata* ethanolic extract (9 L)
*Viscum álbum* ethanolic extract (8 L)
*Coriandrum sativum* ethanolic extract (8 L)
Naphthoxyacetic acid (1.5 kg)
6 Benzylaminopurine (2.5 kg)
Salicylic acid (17 kg)
*Eucalyptus globulus* methanolic extract (8 L)
Premix 2:
*Syzygium aromaticum* oil (7.5 L)
*Cinnamomum zeylanicum* oil (7.5 L)
*Lippia graveolens* oil (7.5 L)
*Larrea tridentata* acetone extract (9 L)
Premix 3:
*Euphorbia antisyphilitica* hexane extract (8 L)
*Jatropha dioica* hexane extract (8 L)
*Agave americana* L crust Hexane extract (7.5 L)
Sodium lauryl sulfate (85 kg)

Once the plant growth and development, inductive resistance bio-stimulant formulation for phytopathogen virus disease control is obtained, it is then properly packaged and stored for use. Performance tests were then conducted from this formulation against several phytopathogen viruses corresponding to the following examples.

Example 2

Antiviral Activity of the Formulation Against PRSV Virus in Papaya

PRSV papaya ringspot virus (Papaya Ringspot Virus) is a virus which genome is single-chain RNA. In order to evaluate the effectiveness of the subject formulation of this invention in PRSV virus control, papaya var. Maradol one-year old plants were used, with PRSV symptoms, to which a random diagnosis by ELISA technique was conducted on them to corroborate the presence of virus. Three formulation doses at 0.50, 0.75 and 1.00 L/ha and an absolute control (without application) were evaluated. Three successive applications spaced 7 days were carried out. Applications were carried out with a 15-L capacity backpack, with 500 L/ha water flow.

Experimental design was totally randomized with 12 repetitions and the experimental unit was one plant. The plantation frame was at a 3.0 m distance between rows and 2.0 m between plants, with a density of 1.670 plants/ha.

In order to evaluate the severity five evaluations were carried out, first one at the time of the first application and the following at 7-day intervals. In every date the severity of the disease of each plant was registered, according to the propose scale by Rivas-Valencia et al., (2003):
1=Healthy Plant.
2=Beginning of symptoms (speckled yellow, some oily spots little defined).
3=Well defined symptoms, not generalized in the leaves, oily stain defined.
4=Severe symptoms generalized in the leaves, concentric ring in fruits.
5=Very severe symptoms, concentric ring in fruits and foliar lamina reduction.
6=Very severe with growth halting and plant death.

With this nominal qualification of plant severity, the population severity index was obtained when applying the following formula:

$$IS = \frac{\sum X_{ki}(N_{ki})}{N_j}$$

Where:
Is=severity index;
Xki=level of damage at time i;
Nki=number of plants with the level of damage at time i, and
Nj=total number of evaluated plants.

Severity index values were converted into percentage in order to fit them and analyze the curve behavior. The results were analyzed by means of the analysis of variance and comparison of Tukey means ($\propto=0.05$).

Figure 2:
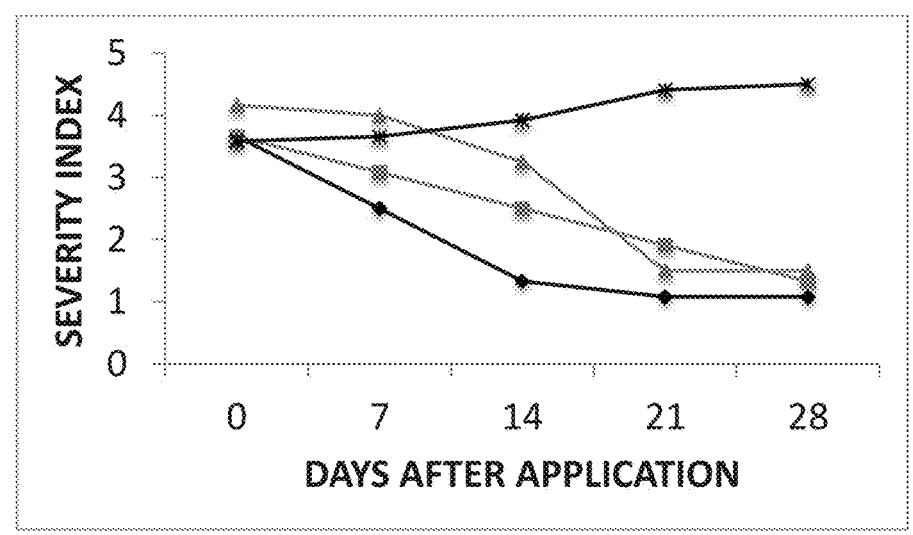
FIG. 2 shows a graph describing the effect of the subject formulation of the present invention on severity index of the papaya annular virus (PRSV) in papaya plants var. Maradol with formulation treatments at diverse doses: the line with marker ⋯※⋯ represents a dose of 0.50 L/ha; the line with marker ⋯▓⋯ represents a dose of 0.70 L/ha; whereas the line with marker ⋯✴⋯ represents a dose of 1.00 L/ha. These observations were carried out with respect to a control without any application ⋯✢⋯.

PRSV-P virus control strategy with the use of the subject formulation of this invention was successful, since it managed to decrease the final virus severity in the plantation by 64% for treatments 1 and 2 (high and intermediate dose, 1.00 and 0.75 L/ha, respectively) and by 70% for treatment 3 (lower dose 0.50 L/ha), whereas the treatment without application (control) increased by 25% in disease severity (FIG. 2). The disease severity values showed significant differences with respect to the control from the second application of product at any dose.

As being apparent from FIG. 2, the remission of symptoms was observed after 14 days (after two applications) in the lowest dose treatment (0.50 L/ha), and there was a disease decrease with 0.75 L/ha treatment. From the fourth evaluation (after three applications) remission of symptoms commenced to be observed in papaya plants at 1.00 L/ha and 0.75 L/ha doses and in the fifth evaluation the remission of symptoms was noticed in three treatments with product doses, without showing significant differences at this time among them. The control on the other hand increased its severity index by 25%.

Figure 3:
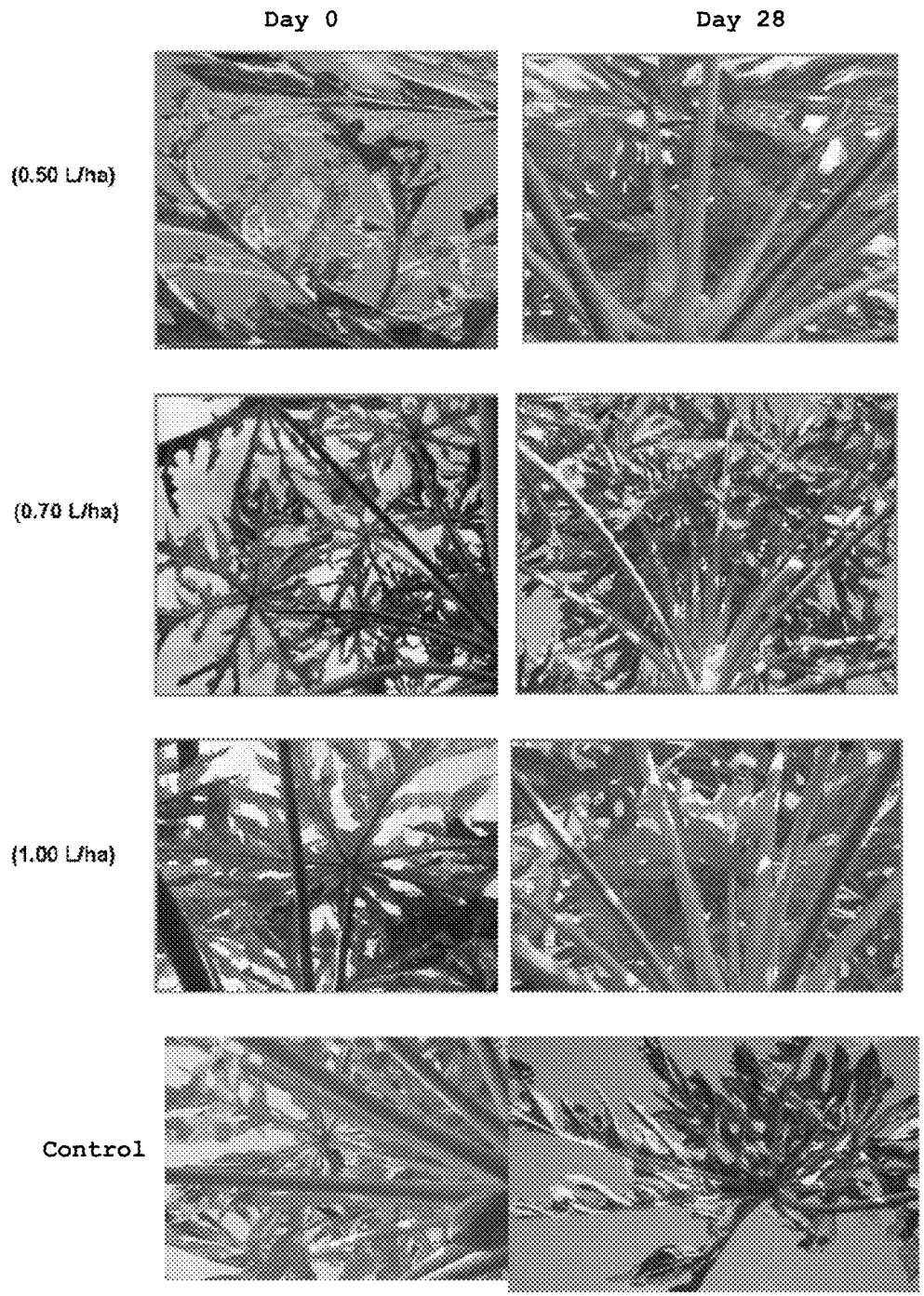
FIG. 3 shows photographs of the aerial parts of papaya plants var. Maradol in field, infected by papaya annular virus (PRSV), to compare the severity index before (Day 0) and after treatment (Day 28) with the subject formulation of the invention at diverse doses (0.50, 0.70 and 1.00 L/ha) with respect to a control without any application.

These results are consistent with those observed in the images from FIG. 3, where a total remission of symptoms occurs 28 days after treatment if three successive applications between 0.50 and 1 L/ha are used at least every 7 days, but not occurring in the control. Additionally, none of the applied doses of the formulation showed toxicity effect for papaya crop during the study.

Example 3

Formulation Activity as Pepper Virosis Resistance Inducer at Greenhouse

Pepper is one of the horticultural plants which has implacably undergone the incidence of viral etiology diseases. In order to demonstrate that the subject formulation of this invention can decrease virosis damage and induce plant resistance, a qualitative study was conducted on pepper plants showing virosis symptoms. The test consisted of application of the formulation in an initial 0.70 L/ha dose, followed by a second application 5 days later at the same dose; a third and fourth application were then conducted at a 0.40 L/ha dose, but with a spacing of ten days among them. Applications were carried out with a backpack, with a 15-liter capacity.

Figure 4:
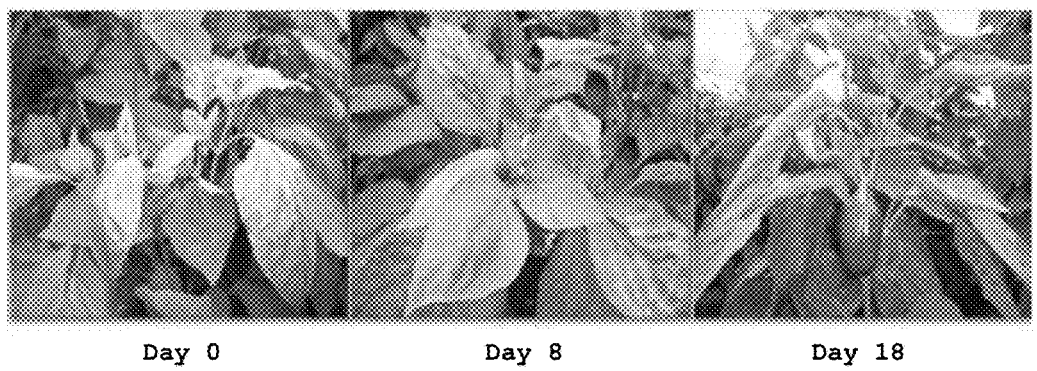
FIG. 4 shows photographs of pepper plants with virosis symptoms in field, before (Day 0) and after the application of the subject formulation of the present invention (Day 8 and Day 18) at smaller doses of 1.00 L/ha.

The effect of the formulation on pepper plants with virosis symptoms was positive and it was observed 8 days after treatment, improving towards day 18 after the first application (FIG. 4). This indicates that the application of the foliar formulation through doses smaller than 1.00 L/ha and with application every 5 days is effective to induce systemic resistance in plants with symptoms caused by viral agents from the second application. The application of the subject formulation of the present invention allows plants to continue their normal development without showing toxicity effects on pepper crop.

Example 4

Formulation Performance Against TYLCV, Yellow Leaf Tomato Virus

Effectiveness of the subject formulation of the present invention was evaluated to induce spoon virus resistance, or TYLCV (Tomato yellow leaf curl virus), during the phase of vegetative growth of a tomato crop developed under semi-arid climate greenhouse. TYCLV virus is a DNA type virus and is transmitted by a population of white fly denominated *Bemisia tabaci*, hemiptera species of the Aleyrodidae family.

Tests were carried out in a multi-tunnel type greenhouse with a surface of 420 m$^2$ having passive lateral and zenithal ventilation by means of windows, with automated opening and closing system. The greenhouse includes a sanded soil, formed by provided earth layer with 30 cm thickness placed on the original property soil, and covered by a manure layer with about 3 cm thickness where a fine sand layer of 10 cm thickness is placed as padding. A drip irrigation facility is provided for crop irrigation and fertilization, with dropper-carrier branches located at twin lines with a distance of 1.2 ms between twin line dropper pairs and 0.8 m between two pairs of adjacent dropper lines, and with emitters within the dropper-carrier branch itself every 50 cm. Drip irrigation installation has auto-compensating droppers with a unitary volume of 3 liters hour$^{-1}$ dropper$^{-1}$. For fertigation programming, an irrigation programmer and 5 tanks of concentrated nutritious solution are provided. Plantation density used will be 1.5 plants m$^{-2}$.

Five different treatments were analyzed in order to carry out the test. Tests to 90 different tomato plants and by three repetitions were carried out for each treatment, formed each by 30 plants per repetition, each treatment repetition is in random blocks to eliminate possible experimental errors derived from different rates of infection based on weather condition distribution within the greenhouse.

Evaluation is carried out in a four week period where each treatment is applied with a weekly frequency. Two applications previous to plant inoculation with TYCLV virus and then two more were carried out. Performed activities for each treatment are disclosed below:
 Day 0: Transplant
 Day 7: Staking and Deleafing
 Day 9: First treatment application
 Day 14: Deleafing
 Day 16: Second treatment application
 Day 20: Inoculation
 Day 22: Third treatment application
 Day 29: Fourth treatment application
 Day 35: Sampling of growth parameters The methodology that was used for crop inoculation is described below: once the crop was settled (20 days after transplant) a population of *Bemisia tabaci* (TYCLV virus carrier) insect plague was inoculated, for which a plant of tomato infected by TYCLV virus and a population of white fly adults ad libitum were introduced inside the greenhouse, next to each experimental parcel. In this way, inoculation of tomato crop by TYCLV virus was promoted during a 5-day period, period during which this infected plant material remained inside the greenhouse. After this period, this plant material was removed from the greenhouse.

Applied treatments are described below:
 Treatment 1: Positive control of plants without infection;
 Treatment 2: Plants with periodic applications with a commercial product widely used in the study zone at manufacturer's recommended dose (REzist® 2 mL/L);
 Treatment 3: Plants with periodic applications of the subject formulation of the present invention at a 2.50 mL/L dose by plant;
 Treatment 4: Plants with periodic applications of the subject formulation of the present invention at a 3.75 mL/L dose by plant;
 Treatment 5: Plants with periodic applications of the subject formulation of the present invention at a 5.00 mL/L dose by plant.

Sampling of growth parameters, subsequent to the fourth treatment application, consisted of measurement of two characteristics: plant height and the number of developed leaves. This measurement was performed in a parcel by repetition and treatment, formed by five plants by parcel. In this way an identification of the plants that undergo growth alterations is possible, resulting from having showed the usual TYCLV virus group of symptoms.

Figure 5:
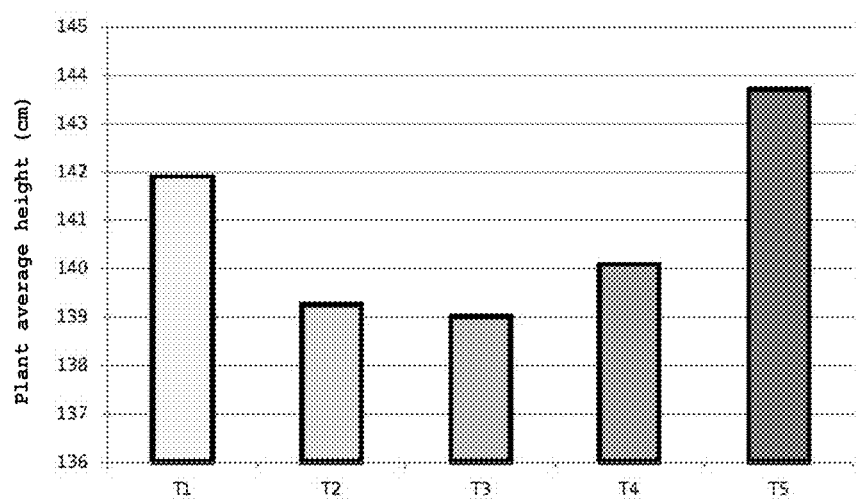
FIG. 5 shows a comparative graph of the average height of tomato plants as growth parameter for diverse treatments. T1: positive control; T2: commercial control at 2 mL/L doses by plant; T3, T4 and T5: treatment with the subject formulation of the present invention at doses of 2.50 mL/L, 3.75 mL/L and 5.00 mL/L by plant, respectively.

The results of the growth parameters with respect to the plant height are outlined in FIG. 5, where it is possible to observe that from the application of a dose greater than 3.75 m/L by plant of the subject formulation of the present invention (Treatments 4 and 5) a better development of the tomato plant height infected with TYCLV virus is obtained compared to that from the commercial control (Treatment 2). A 5.00 mL/L dose is emphasized in which the plant height development is even greater than in the positive control, indicating the plant growth and development bio-stimulant activity and inductive resistance for phytopathogen virus disease control of the formulation.

Figure 6:
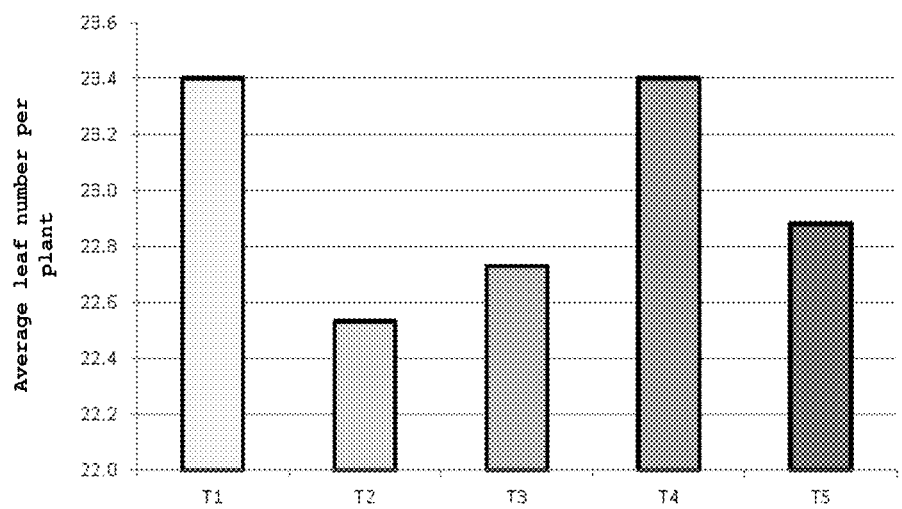
FIG. 6 shows a comparative graph of the average number of leaves for tomato plant as growth parameter for diverse treatments. T1: positive control; T2: commercial control at doses of 2 mL/L by plant; T3, T4 and T5: treatment with the subject formulation of the present invention at doses of 2.50 mL/L, 3.75 mL/L and 5.00 mL/L by plant, respectively.

As far as the growth parameter results concerning the number of leaves developed by plant in each treatment, it was possible to identify that the subject formulation of the present invention at any dose allows a greater development of leaves by plant than the commercial control (FIG. 6); and in case of an application at a 3.75 mL/L dose by plant, the formulation has similar performance to positive control, this again indicates the activity of the formulation as plant growth and development and inductive resistance bio-stimulant for phytopathogen virus disease control.

Example 5

Activity of the Formulation as Inducer of Resistance to Virosis of Tomato and Pepper at Field Level In order to demonstrate that the subject formulation of this invention can decrease virosis damage and induce resistance in plants, a study was performed on tomato and pepper plants at field level where virosis symptoms were present. The test consisted of the application of the formulation in a dose of 0.5 L/ha in soil and four applications were later carried out by foliar route with a spacing of seven days among them. Applications were carried out with a backpack, with capacity of 15 liters. Tomato and pepper plants without the application of the formulation of the present invention were taken into account as control. Viral incidence percentage was determined by means of a visual observation of damage caused in tomato and pepper crop plants at field level.

Figure 7:
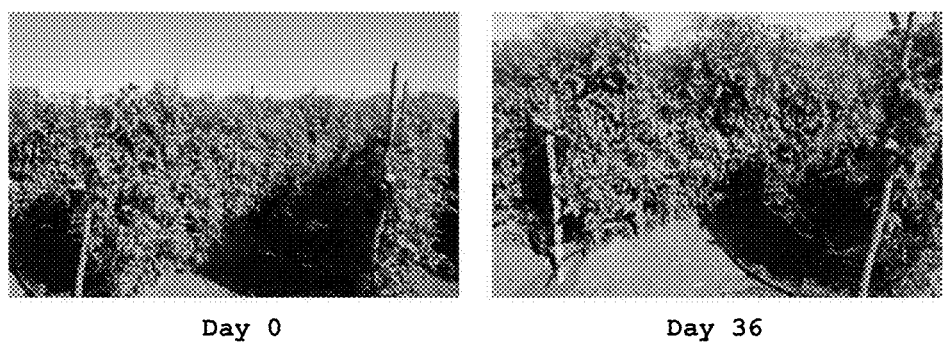
FIG. 7 shows photographs of tomato crop plants not treated with the formulation of the present invention at beginning (Day 0) and 36 days after evaluation at field level.
Figure 8:
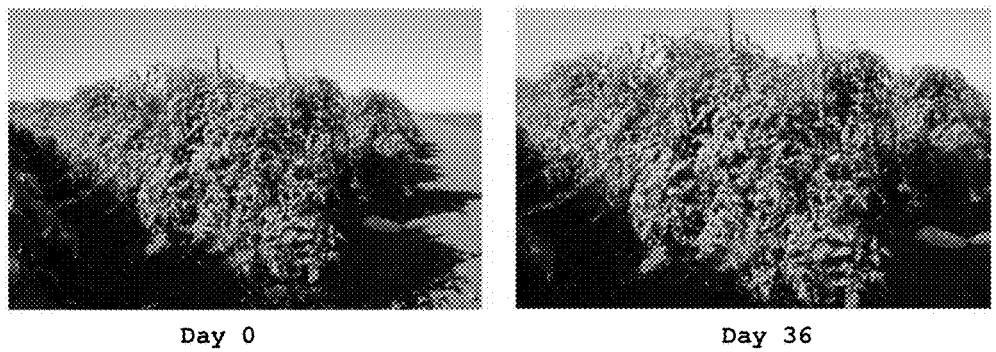
FIG. 8 shows photographs of tomato crop plants treated with the formulation of the present invention at beginning (Day 0) and 36 days after evaluation at field level.

The effect of the formulation on tomato crop plants with virosis symptoms was positive and at the beginning of the evaluation a viral incidence of 31% was observed and after 36 days of the treatment it then decreased down to 8.7% where plants presented a vigorous foliage yield (FIG. 8). Tomato crop plants that were not treated with the formulation of the present invention presented a smaller viral incidence of 7.3% at the beginning of the evaluation, but 36 days later they showed greater damage in the yield and plant foliage (FIG. 7).

Figure 9:
FIG. 9 shows photographs of pepper crop plants not treated with the formulation of the present invention at the beginning (Day 0) and 36 days after evaluation at field level.
Figure 10:
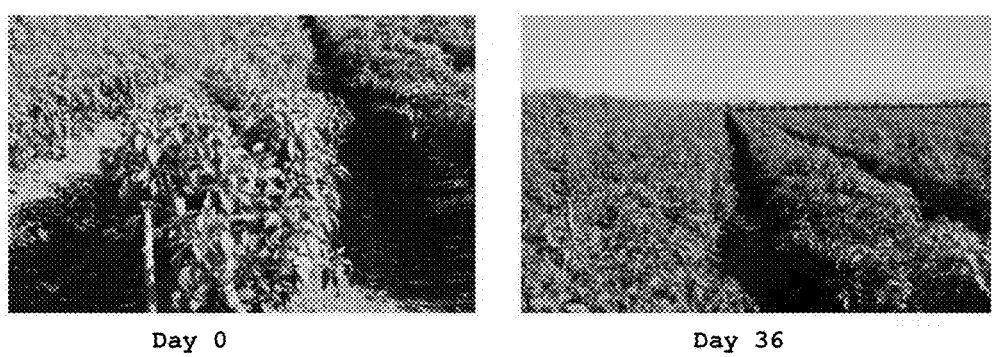
FIG. 10 shows photographs of pepper crop plants treated with the formulation of the present invention at the beginning (Day 0) and 36 days after evaluation at field level.

The results of the formulation on pepper crop plants also were positive, where at the beginning of the evaluation a viral incidence of the 11% was observed and at 36 days from treatment it decreased until 5.7% showing a greater foliage yield (FIG. 10). It was observed that pepper crop plants that were not treated with the formulation of the present invention showed a tendency similar to those of tomato, because at the beginning of the evaluation they showed a smaller viral incidence of 7.2%, but 36 days later they showed greater damage in yield and plant foliage (FIG. 9).

This indicates that the application of the formulation in soil and then by foliar route with a dose of 0.5 L/ha every 7 days is effective to induce systemic resistance in tomato and pepper crop plants at field level with symptoms caused by viral agents. The application of the subject formulation of the present invention allows that plants continue their normal development without showing toxicity effects on tomato and pepper crop plants at field level.

Example 6

Molecular Detection of DNA Virus in Tomato and Pepper Crop Plants

In order to demonstrate that the subject formulation of the present invention can decrease virosis damage and induce resistance in plants, a study was performed to molecularly detect the presence of Begomovirus genus DNA virus in tomato and pepper plants at field level. Firstly, tomato and pepper seeds were washed with 70% ethanol during two minutes and 30% chlorine during 15 minutes, then washed with distilled sterile water and placed in trays with substrate for its germination in greenhouse.

After three to four weeks subsequent to the germination the tomato and pepper plants were inoculated with Begomovirus genus DNA virus (Tomato yellow leaf curl virus (TYLCV) and Pepper Huasteco yellow vein virus (PHYVV)) by agroinfiltration by inoculating 2 ml of DNA. Application of the formulation of the present invention was carried out five days after seed inoculation having used a dose of 0.5 L/ha.

Figure 11:
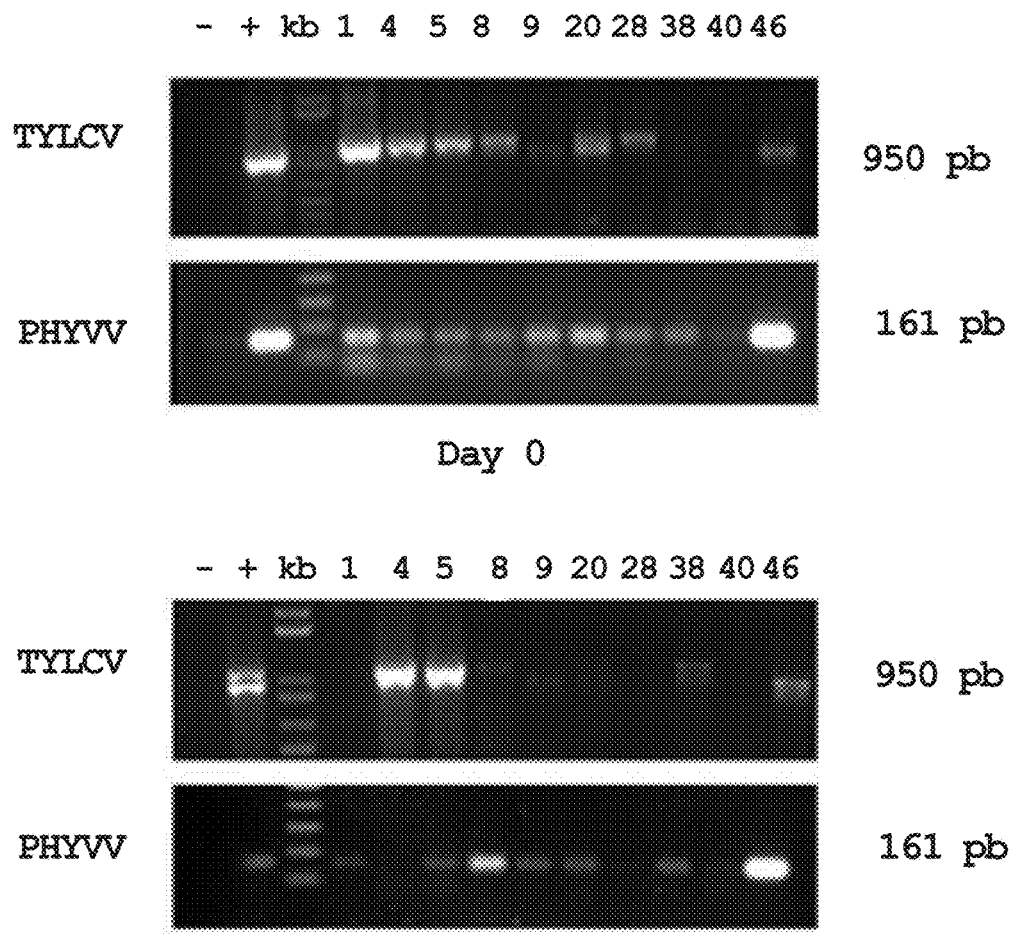
FIG. 11 shows images of agarose gel electrophoresis of the DNA virus detection analysis of Begomovirus genus (Tomato yellow leaf curl virus (TYLCV) and Pepper Huasteco yellow vein virus (PHYVV)) in tomato crop plants at the beginning (Day 0) and 36 days after evaluation.
Figure 12:
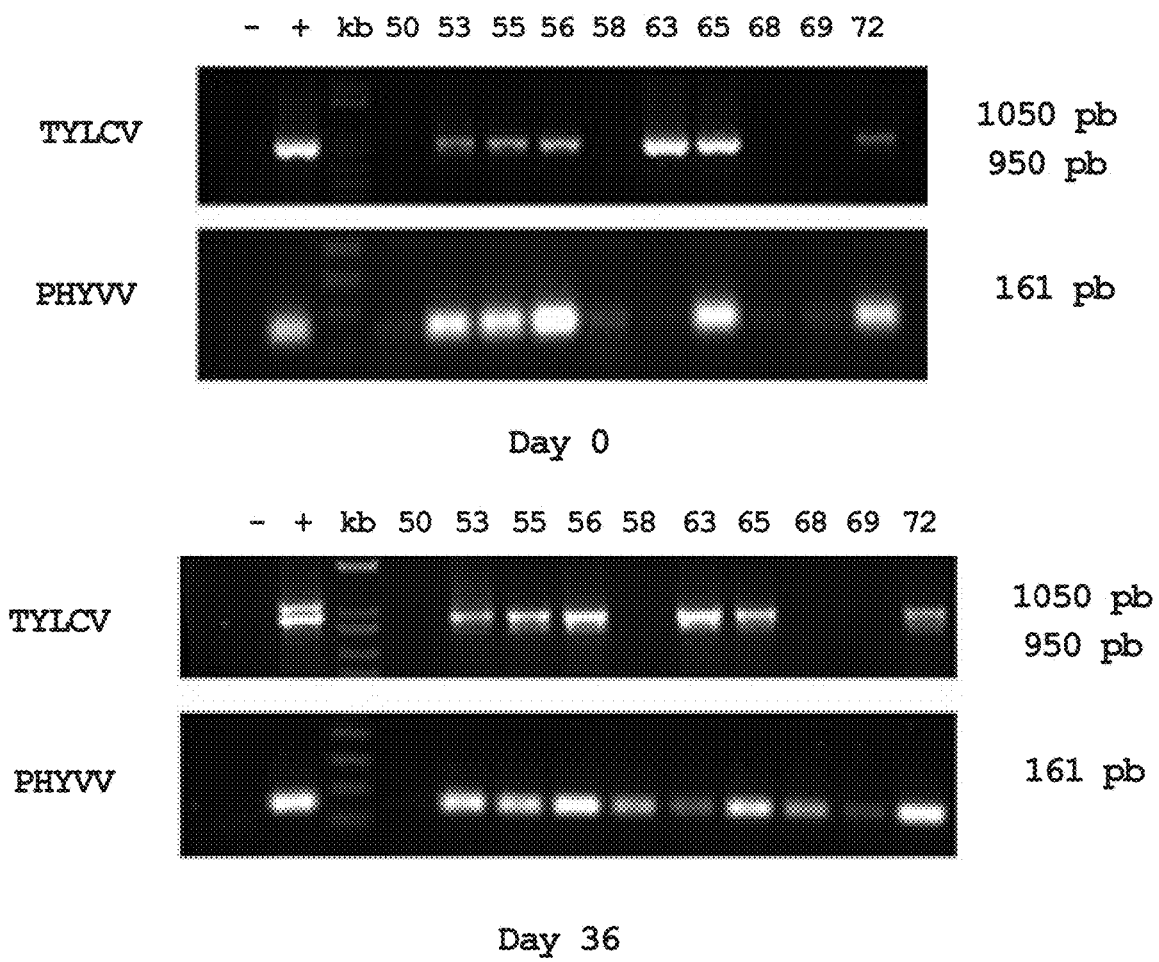
FIG. 12 shows images of agarose gel electrophoresis of DNA virus detection analysis of Begomovirus genus (Tomato yellow leaf curl virus (TYLCV) and Pepper Huasteco yellow vein virus (PHYVV)) in pepper crop plants at the beginning (Day 0) and 36 days after evaluation.

Molecular detection of the TYLCV and PHYVV viruses was carried out at the beginning of the application (Day 0) and at 36 days after application of the formulation of the present invention. Firstly, an individual DNA extraction from apical leaves of each tomato and pepper crop plant was carried out based on CTAB methodology at 3% (Zhang et al., 1998). Later a semi-quantitative molecular detection by polymerase chain reaction (PCR) was performed, with the idea to analyze indirectly the degree of virus replication. Amplified products are shown in images by 1% agarose gel electrophoresis (FIG. 11 and FIG. 12).

The results obtained in the 1% agarose gel electrophoresis images demonstrated that Begomovirus genus DNA virus (Tomato yellow leaf curl virus (TYLCV) and Pepper Huasteco yellow vein virus (PHYVV)) molecular detection in tomato crop plants was qualitatively smaller at 36 days from evaluation compared to an initial comparison of the evaluation (Day 0) (FIG. 11), whereby the formulation of the present invention prevented progress of viral group of symptoms improving foliage yield of tomato crop plants at field level.

Images of 1% agarose gel electrophoresis demonstrated that Begomovirus genus DNA virus (Tomato yellow leaf curl virus (TYLCV) and Pepper Huasteco yellow vein virus (PHYVV)) molecular detection in pepper plants continued until 36 days from evaluation (FIG. 12), nevertheless the formulation of the present invention also managed to avoid the progress of viral group of symptoms improving foliage yield of pepper crop plants at field level.

Example 7

Molecular Detection of RNA Virus in Tomato and Pepper Crop Plants at Field Level In order to demonstrate that the subject formulation of the present invention can decrease virosis damage and induce resistance in plants, a study was performed to molecularly detect the presence of Torradovirus genus (ToMarV) RNA virus in tomato and pepper plants at field level. Firstly, tomato and pepper seeds were washed with 70% ethanol during two minutes and 30% chlorine during 15 minutes and then washed with distilled sterile water and placed in trays with substrate for greenhouse germination.

After three to four weeks from germination, tomato and pepper plants were inoculated with Torradovirus genus (ToMarV) virus by inoculating 2 ml of DNA through agroinfiltration. Application of the formulation of the present invention was performed five days from seed inoculation having used a dose of 0.5 L/ha.

Molecular virus detection was carried out at the beginning of application (Day 0) and at 36 days after application of the formulation of the present invention. Firstly, an individual extraction of symptomatic foliar tissue RNA from each tomato and pepper plant was carried out according to the protocol described by Singh (2002) modified with sodium sulfite. Then, the molecular detection by polymerase chain reaction (PCR) with specific primers (ToMarV-F/ToMarV-R primers (Verbeek et al., 2008) which amplify a 511pb fragment) for each virus was performed.

In order to increase sensitivity in ToMarV detection a nested PCR was performed using pJER-1123 and pJER-1124 primers (Camacho et al., 2015), which amplifies a 332 pb fragment using the DNA obtained during the first PCR as a template or mold. Nested PCR product was visualized by 1% agarose gel electrophoresis (FIG. 13 and FIG. 14).

The images of 1% agarose gel electrophoresis demonstrated that the simple and nested molecular detection of Torradovirus genus (ToMarV) RNA virus in tomato plants continues until 36 days from evaluation (FIG. 13), however the formulation of the present invention managed to avoid the progress of viral group of symptoms improving foliage yield of tomato crop plants at field level.

Figure 14:
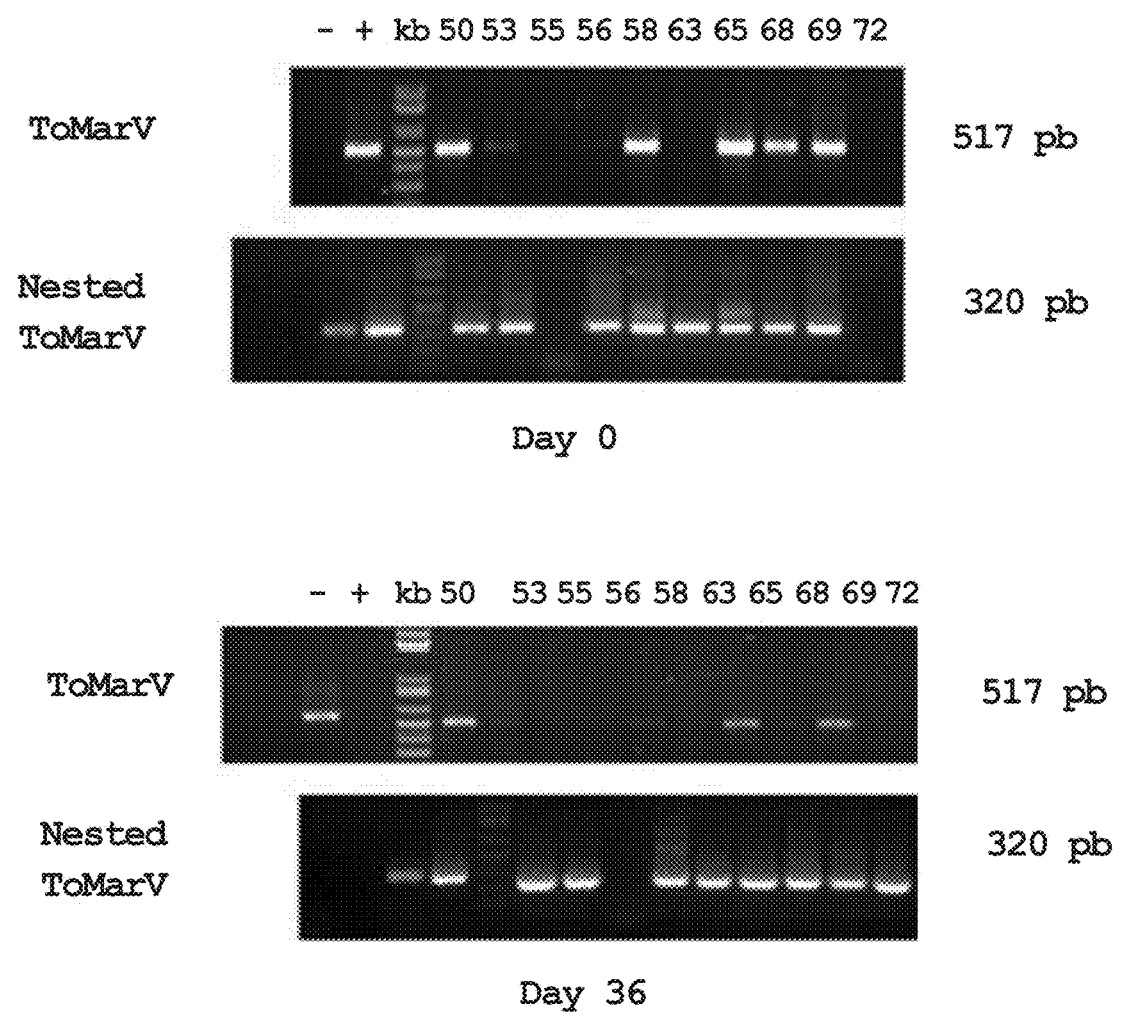

Results obtained in images of 1% agarose gel electrophoresis demonstrated that the nested molecular detection of the Torradovirus genus (ToMarV) RNA virus in pepper plants was similar at the beginning (Day 0) and 36 days from evaluation (FIG. 14). And a single molecular detection of Torradovirus genus (ToMarV) RNA virus was qualitatively smaller at 36 days from evaluation compared to initial time of evaluation (Day 0) (FIG. 14), whereby the formulation of the present invention managed to avoid the rate of virus replication and the progress of viral group of symptoms and improving the foliage yield of pepper crop plants at field level.

The invention claimed is:

1. A plant growth and development, inductive resistance bio-stimulant formulation comprising a homogeneous mixture obtained by the following process
preparing a first base formulation comprising adding in sequential order the following elements in purified water under constant stirring
aqueous extract of *Rosmarinus officinalis,*
aqueous extract of peppermint,
aqueous extract of *Salvia officinalis,*
soymilk,
egg white,
*Aloe vera* gel,
sulfathiazole,
phenylalanine, and
calcium thiosulfate;
separately, preparing a first premix comprising ethanolic plant extracts, hormones and plant growth regulators;
adding the first premix to the first base formulation under constant stirring to obtain a first premix-base formulation, thereafter adding methanolic extract of *Eucalyptus globulus* to the first premix-base formulation under constant stirring to obtain a second base formulation;
separately, preparing a second premix comprising absolute oils of plants;
adding the second premix to the second base formulation under constant stirring to obtain a second premix-base formulation, thereafter adding *Larrea tridentata* acetone extract to the second premix-base formulation under constant stirring to obtain a third base formulation;
separately, preparing a third premix comprising hexane extracts; and
adding the third premix and sodium lauryl sulfate to the third base formulation under constant stirring to obtain the plant growth and development, inductive resistance bio-stimulant formulation.

2. The formulation of claim 1, wherein the ethanolic plant extracts are selected from the group consisting of ethanolic extract of *Larrea tridentate*, ethanolic extract of *Viscum album*, ethanolic extract of *Coriandrum sativum*, the hormones are selected from the group consisting of auxins, gibberellins, salicylic acid, jasmonates, and the plant growth regulator is selected from the group consisting of 6 benzylaminopurine and naphthoxyacetic acid.

3. The formulation of claim 1, wherein the absolute oils of plants are derived from plants selected from the group consisting of *Syzygium aromaticum, Cinnamomum zeylanicum, Eucalyptus globulos, Rosmarinus officinalis, Salvia officinalis,* peppermint and *Coriandrum sativum.*

4. The formulation of claim 1, wherein the hexane extracts are selected from the group consisting of *Euphorbia antisyphilitica* hexane extract, *Jatropha dioica* hexane extract and *Agave americana* L hexane extract.

5. The formulation of claim 1, wherein in the first base formulation the elements are present in a concentration having the following ranges aqueous extract of *Rosmarinus officinalis* 0.75-1.25% v/v based on the final formulation; aqueous extract of peppermint 0.75-1.25% v/v based on the final formulation; aqueous extract of *Salvia officinalis* 0.75-1.25% v/v based on the final formulation; soymilk 1.5-2.5% v/v based on the final formulation; egg white 0.75-1.25% v/v based on the final formulation; *Aloe vera* gel 0.75-1.25% v/v based on the final formulation; sulfathiazole 0.375-0.625% w/v based on the total volume of the final formulation; phenylalanine 0.75-1.25% w/v based on the total volume of the final formulation; and calcium thiosulfate 15.0-25.0% w/v based on the total volume of the final formulation.

6. The formulation of claim 1, wherein in the first premix the ethanolic plant extracts hormones and plant growth regulators are present in a concentration having the following ranges ethanolic extract of *Larrea tridentata* 0.75-1.25% v/v based on the final formulation, ethanolic extract of *Viscum album* 0.75-1.25% v/v based on the final formulation, ethanolic extract of *Coriandrum sativum* 0.75-1.25% v/v based on the final formulation, naphthoxyacetic acid 0.15-0.25% w/v based on the total volume of the final formulation, 6-Benzylaminopurine 0.225-0.375%w/v based on the total volume of the final formulation, and salicylic acid 1.5-2.5% w/v based on the total volume of the final formulation.

7. The formulation of claim 1, wherein the methanolic extract of *Eucalyptus globulus* ranges 0.75-1.25% v/v of the final formulation.

8. The formulation of claim 1, wherein the absolute oils of plants are selected from the group consisting of *Syzygium aromaticum* oil, *Cinnamomum zeylanicum* oil and *Lippia graveolens* oil.

9. The formulation of claim 1, wherein the absolute oils of plants are present in a concentration having the following ranges *Syzygium aromaticum* oil 0.75-1.25% v/v based on the final formulation, *Cinnamomum zeylanicum* oil 0.75-1.25% v/v based on the final formulation and *Lippia graveolens* oil 0.75-1.25% v/v based on the final formulation.

10. The formulation of claim 1, wherein the acetone extract of *Larrea tridentata* is present in a concentration ranging 0.75-1.25% v/v based on the final formulation.

11. The formulation of claim 4, wherein in the third premix the hexane extracts are present in a concentration having the following ranges *Euphorbia antisyphilitica* hexane extract 0.75-1.25% v/v based on the final formulation, *Jatropha dioica* hexane extract 0.75-1.25% v/v based on the final formulation, *Agave americana* L crust hexane extract 0.75-1.25% v/v based on the final formulation.

* * * * *